United States Patent [19]

Hirshowitz

[11] Patent Number: 4,896,680
[45] Date of Patent: Jan. 30, 1990

[54] METHOD OF EXTENDING A FLAP OF SKIN

[76] Inventor: Bernard Hirshowitz, 55 Margalit Street, Mount Carmel, Haifa, Israel

[21] Appl. No.: 150,673

[22] Filed: Feb. 1, 1988

[30] Foreign Application Priority Data

Feb. 10, 1987 [GB] United Kingdom ............... 8702983

[51] Int. Cl.$^4$ ............................................. A61B 17/04
[52] U.S. Cl. ...................................................... 606/218
[58] Field of Search ................. 128/20, 303 R, 334 C, 128/334 R, 335, DIG. 26, 898; 604/174, 178; 24/161

[56] References Cited

U.S. PATENT DOCUMENTS

| | | | |
|---|---|---|---|
| 361,886 | 4/1887 | Nichols | 24/161 R |
| 1,497,722 | 1/1923 | Holst-Grubbe | 604/178 |
| 3,542,015 | 11/1970 | Steinman . | |
| 3,730,187 | 5/1973 | Reynolds | 128/DIG. 26 |
| 3,825,010 | 7/1974 | McDonald | 604/174 |
| 3,971,384 | 7/1976 | Hasson | 128/335 |

FOREIGN PATENT DOCUMENTS

0079205  5/1983  European Pat. Off. .

*Primary Examiner*—Michael H. Thaler
*Assistant Examiner*—William Lewis
*Attorney, Agent, or Firm*—Pollock, Vande Sande and Priddy

[57] ABSTRACT

A method of applying force to the skin such as to for use in stretching the skin by load cycling, or for use as a surgical retractor, utilizes an apparatus that comprises two pins or hooks that are joined together by a flexible nylon strap. The strap has rectangular apertures separated by lateral bars. One end of the strap is riveted to one pin while the other end of the strap is passed through a ratchet locking device mounted on the other pin. In use, one pin is fastened to a loose flap of skin and the other pin is fastened to another site on the skin surface. The free end of the strap is then pulled through the locking device, which holds it against movement in the opposite direction, until the desired tension is applied, the skin under tension is allowed to creep and extend in length, and the free end of the strap is then pulled further through the locking device to reapply tension to the skin.

2 Claims, 2 Drawing Sheets

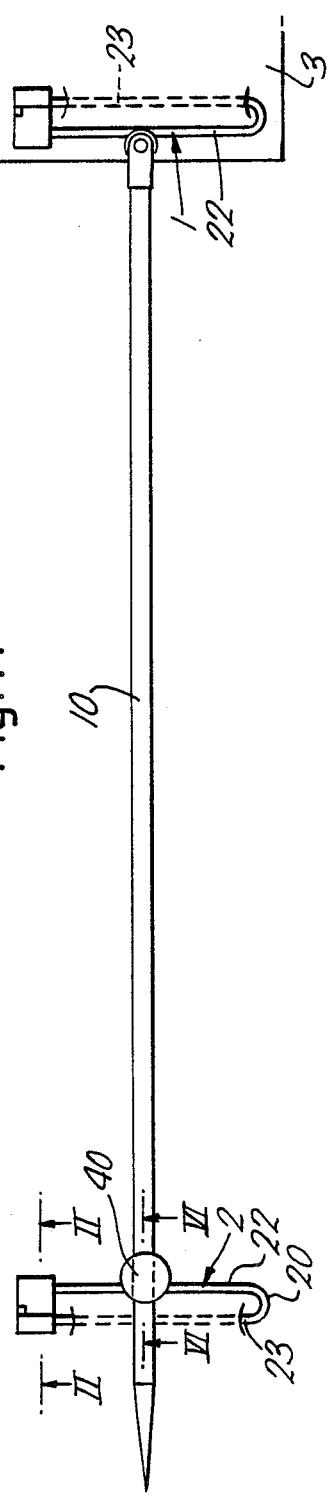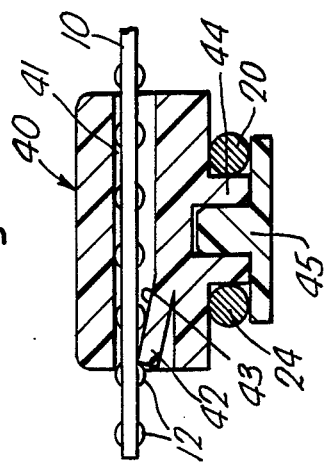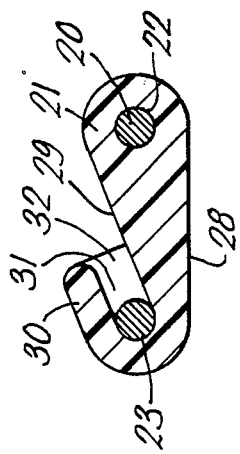

METHOD OF EXTENDING A FLAP OF SKIN

BACKGROUND OF THE INVENTION

This invention relates to surgical apparatus for applying force to the skin and is more particularly concerned with a method of load cycling a flap of skin to extend the length of said flap.

It has been found that, when a constant stretching force is applied to skin, the skin will stretch continuously. This creep of the skin is effected partly by extrusion of tissue fluid from between the collagen fibres as they align themselves in the direction of the stretching force, and parallel to each other. Up to 90% of the dry weight of the dermis is constituted by collagen fibres which have a highly convoluted arrangement when the skin is in a state of rest.

Initially, the rearrangement of collagen fibres is accomplished with ease, under low loads. As more of the collagen fibres become aligned, a greater stretching force is required to overcome the increased tension of the skin. Care, however, must be taken to avoid excessive stretching which can cause damage to the skin.

Additionally extensibility of the skin can be obtained by load cycling. With this method, tension is applied to the skin for several periods separated by intervals of relaxation. Each time that tension is applied, more collagen fibres are aligned in the direction of the stretching force and additional extension is produced. Typically, tension can be applied three or four times for three to four minutes each with the periods of tension application being separated by relaxation intervals of about a minute.

This technique can be used to close skin defects, such as produced by burn injury, in a relatively short time and with less discomfort than some previous techniques.

BRIEF SUMMARY OF THE INVENTION

It is an object of the present invention to provide a method and apparatus that can be used to apply traction to the skin or that can be used to apply a force to the skin to hold it in a retracted position, such as during surgery.

According to one aspect of the present invention there is provided surgical apparatus for applying force to the skin, the apparatus comprising first and second retaining means adapted to retain different respective regions of the skin, flexible strap means secured between said first and second retaining means, and locking means arranged to retain the strap means against forces tending to separate the two retaining means, but to allow the length of the strap means between the two retaining means to be shortened.

The locking means preferably includes means bearing resiliently on the strap means to allow displacement of the strap means in one direction and not in the opposite direction. The strap means preferably has lateral bars and the means bearing resiliently on the strap means contacting the bars of the strap means. The locking means have a passage therethrough within which is located a resilient tongue with an inclined surface over which the bars on the strap can slide in one direction. The locking means may be mounted on one of the retaining means.

The retaining means may include a pin adapted to be pushed through and under the skin surface. The pin is preferably of generally U-shape having two parallel limbs, one limb having clip means mounted at one end and the other limb having a sharpened point adapted to be pushed through the skin surface, the sharpened point being engageable with the clip means. One of the limbs may be formed in a loop at a point along its length, the strap means being secured at one end to a loop in one of the retaining means. The locking device may be secured to a loop in the other of the retaining means.

Alternatively, the retaining means may include at least one prong that curves downwardly into the skin, the or each prong on the two retaining means pointing towards one another.

Skin traction apparatus and its method of use, according to the present invention, will now be described, by way of example, with reference to the accompanying drawings.

BRIEF DESCRIPTION OF DRAWINGS

FIG. 1 is a plan view of the apparatus in use;

FIG. 2 is an enlarged sectional view along the line II—II of a part of the apparatus;

FIG. 6 is a sectional view of the locking device of the apparatus, along the line VI—VI of FIG. 1;

DETAILED DESCRIPTION

Figure 3:
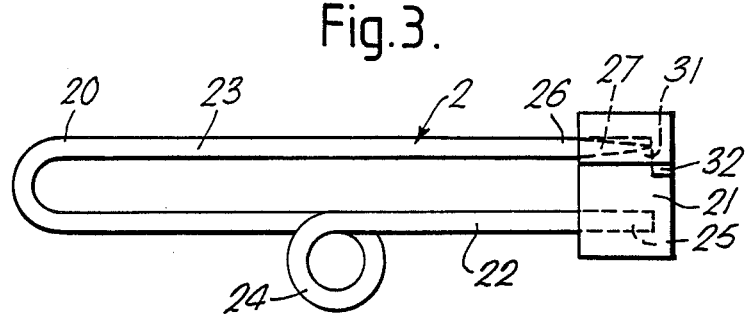
FIG. 3 is an enlarged plan view of a retaining pin of the apparatus.

With reference first to FIGS. 1 to 6, the apparatus has two pins 1 and 2, or other retaining devices, connected together by a strap 10 of adjustable length. One pin 1 is secured to a loose flap of skin 3, the other pin 2 being anchored firmly to another site on the skin surface by piercing the skin and subdermal tissue. Traction is applied to the loose flap of skin 3 by incrementally shortening the length of the strap 10 between the two pins 1 and 2.

The two pins 1 and 2 have the same form of construction, comprising a U-shape spring wire 20 of a stainless steel and a moulded clip 21 of plastics material. The wire is 1.5 mm in diameter and is bent into two parallel limbs 22 and 23 of length 50 mm and separation 4 mm. One limb 22 is coiled into a small loop 24 midway along its length and has its free end 25 permanently anchored with the clip 21. The other limb 23 is straight along its length and has its free end 26 sharpened to a cutting point 27, which can be retained or released from the clip 21. The clip 21 has a flat underside 28 and an inclined upper surface 29 that slopes downwardly across the width of the clip. At that edge of the clip 21 where the upper surface 29 is lower, the clip is formed with a lip 30 that overlies the upper surface to form a recess 31 just high enough to receive the sharpened free end 26 of the spring wire 20. The end of the recess 31 away from the spring wire 20 is closed by an end wall 32 to protect the sharp point 27 of the spring wire. The resilience of the spring wire 20 is such that the limb 23 is urged securely into the bottom end of the recess 31 when the limb is held against the upper surface 29 of the clip 21. The limb 23 can be freed from the recess 31 by squeezing the two limbs 23 and 22 together, until the limb 23 is clear of the end of the lip 30, then pushing the limb upwardly over the top of the lip and allowing the resilience of the wire 20 to open the limb beyond the edge of the clip 21. The two pins 1 and 2 differ from one another only in that the free, sharpened limbs of their spring wires are on different sides.

Figure 4:
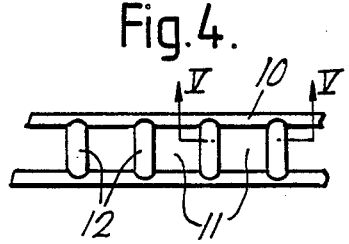
FIG. 4 is an underside view of a strap of the apparatus.
Figure 5:
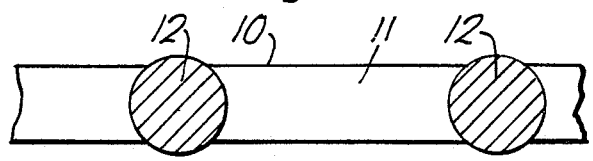
FIG. 5 is a sectional side elevation of the strap of FIG. 4 along the line V—V.

One pin 1 is riveted, through its loop 24, to the underside of one end of the strap 10. The strap 10, which is shown in more detail in FIGS. 4 and 5, is made of a flexible plastics material such as nylon and is of substantially rectangular section being 3.5 mm wide, about 0.8 mm thick and 293 mm long. The strap 10 is perforated along its length with rectangular apertures 11 that are separated from one another by lateral bars 12 of circular section. The diameter of the bars 12 is 1 mm so that they form projections above and below the surface of the strap.

The other end of the strap 10 is retained by a ratchet locking device 40 on the pin 2, as shown in FIG. 6. The locking device 40 is of generally circular section and is an integral, one-piece moulding of a resilient plastics material such as nylon. The locking device 40 has a passage 41 therethrough of rectangular section into which the strap 10 is inserted from the right-hand end. An integral ratchet tongue 42, at the left-hand end of the passage 41 bears resiliently on the underside of the strap 10. The tongue 42 has an inclined upper surface 43 which slopes upwardly to the left thereby allowing the tongue to ride over the bars 12 when the strap 10 is pulled through the locking devide 40 to the left to shorten the length of strap 10 between the two clips 1 and 2. Engagement of the tongue 42 with the bars 12 prevents the strap 10 being pulled through the locking device 40 in the opposite direction, to lengthen the strap. The underside of the locking device 40 is formed with an integral cylindrical stem 44 which has a diameter equal to the internal diameter of the loop 24 of the spring wire 20, the length of the stem 44 being equal to the thickness of the wire. The locking device 40 is retained in the loop 24 of the pin 2 by means of a button 45 of diameter 6 mm that is secured into the stem 44 beneath the loop 24.

In use, a loose flap of skin 3 is formed by the surgeon cutting the skin away from the underlying muscle. The right-hand pin 1 is opened and retained with the skin flap 3 by pushing the sharpened point 27 of the limb 23 through and under the skin flap. The point 27 is then threaded back through the skin to project above the skin surface and the point is pushed into the recess 31 of the clip 21 so that the pin 1 is locked in a closed position. The left-hand pin 2 is retained with a site on the skin surface in a similar way, at a distance of about 150-200 mm from the loose flap of skin 3 to form a secure anchor. The surgeon then pulls the free end of the strap 10 through the locking device 40 to shorten its effective length until the flap of skin 3 is pulled taut and the desired tension is applied.

The skin gradually becomes slack because of creep and, after three or four minutes, the length of strap 10 can be further shortened by again pulling it through the locking device 40 where it will be held by the ratchet tongue 42.

This is repeated several times until no further extension of the skin flap 3 is evident. Typically this load cycling will take some fifteen to thirty minutes.

The pins 1 and 2 are then unfastened and removed from the skin. The extended flap of skin 3 is placed over the defect to be covered and sutured in position.

This device enables a far more rapid extension of skin to be produced than with, for example, silicone bag expansion techniques previously used. As a result, skin expansion that has previously taken many days to achieve can be produced in a single operating session.

Various modifications to the device are possible. The length of the strap between the two pins can be shortened in other ways than by means of a ratchet locking device.

Figure 7:
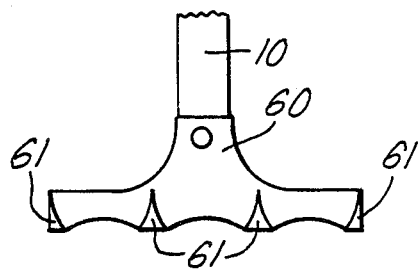
FIG. 7 is a plan view of an alternative retaining device.
Figure 8:
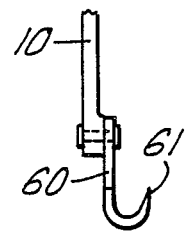
FIG. 8 is a side elevation view of the device of FIG. 7.

Various other forms of retaining means may alternatively be used to retain the skin. For example, as shown in FIGS. 7 and 8, the retaining means could take the form of hooks 60 made from a strip of stainless steel with prongs 61 curved downwardly to a semi-circle of radius about 5 mm. The prongs 61 of the hooks 60 point down and backwardly along the strap 10 towards one another.

The strap need not have apertures but could, for example, have projections in the form of teeth that are engageable by the locking device, or a similar locking device. The width of the strap can lie vertical or parallel to the surface of the skin.

The apparatus could be used as a surgical retractor, to hold skin away from a surgical site so as to enable access for a surgical operation.

The apparatus can be made at relatively low cost so as to be disposable after a single use. Various size apparatus can be made for different applications giving the apparatus great flexibility. The apparatus can be of light weight and of compact construction and is easy to use.

What is claimed is:

1. A method of applying incremental traction to skin to extend a flap of skin comprising the steps of: (a) pushing first and second hooked retaining means into different respective regions of the skin to puncture said different respective regions of the skin; (b) pulling an elongate member that is attached to one of the retaining means through locking means that is attached to the other of said retaining means so as to shorten the length of the elongate member between the two retaining means and thereby apply tension to the skin; (c) allowing the skin to creep and extend in length; (d) thereafter shortening the length of the elongate member between the two retaining means to reapply tension to the skin; (e) withdrawing said hooked retaining means from said different respective regions of the skin a period of time following initiation of step (d); and (f) thereafter placing the extended skin over a defect and suturing it in position to conceal the defect.

2. The method of claim 1 wherein each of steps (b), (c) and (d) is repeated a plurality of times.

* * * * *